United States Patent [19]

Fischler et al.

[11] 4,027,663
[45] June 7, 1977

[54] HEART BEAT DETECTOR

[75] Inventors: Henryk Fischler; Yaakov Krupka, both of Rehovot; Yacov Itzchak, Ramat Efal, all of Israel

[73] Assignee: Yeda Research & Development Co. Ltd., Rehovot, Israel

[22] Filed: Oct. 6, 1975

[21] Appl. No.: 620,224

[30] Foreign Application Priority Data

Oct. 4, 1974 Israel .................................. 45786

[52] U.S. Cl. .......................................... 128/2.06 R
[51] Int. Cl.² .......................................... A61B 5/04
[58] Field of Search ................. 128/2.06 R, 2.06 A, 128/2.06 B, 2.1 Z, 2.1 P, 2.06 F

[56] References Cited

UNITED STATES PATENTS

| | | | |
|---|---|---|---|
| 3,144,019 | 8/1964 | Haber | 128/2.06 A |
| 3,469,115 | 9/1969 | Partridge | 128/2.06 R |
| 3,495,584 | 2/1970 | Schwalm | 128/2.06 B |
| 3,548,807 | 12/1970 | Crovella | 128/2.06 R |
| 3,602,215 | 8/1971 | Parnell | 128/2.06 B |
| 3,612,041 | 10/1971 | Ragsdale | 128/2.06 A |
| 3,613,670 | 10/1971 | Edenhofer | 128/2.06 F |
| 3,721,230 | 3/1973 | Ziernicki | 128/2.06 B |

*Primary Examiner*—Robert W. Michell
*Assistant Examiner*—Lee S. Cohen
*Attorney, Agent, or Firm*—Browdy and Neimark

[57] ABSTRACT

A heart beat detector for use in emergencies and especially under adverse conditions of noise and vibration, of the type adapted to continuously monitor the ECG, extracting the QRS complexes and signalling the occurrence of heart beats by easily perceptible, light signals. The detector includes an inter-electrode impedance sensor; for automatically ascertaining whether adequate conductivity exists between the body of the patient and the electrodes of the detector applied to said body. According to a specific embodiment of the invention the device comprises a sub-system adapted to indicate the activity of the batteries of the instrument, the state of the electrodes and of the other circuits.

5 Claims, 5 Drawing Figures

HEART BEAT DETECTOR

FIELD OF THE INVENTION

The present invention relates to an improved heart-beat detector. More particularly the invention relates to a novel heart-beat detector for use in emergencies and under adverse conditions of noise, vibration and the like. Other and further features of the invention will become apparent hereinafter.

SUMMARY OF THE INVENTION

The novel heart-beat detector operates on the principle of continuous monitoring of the electrical activity of the heart (ECG), extraction of the QRS complexes which signify the contractions of the ventricles (heart beat), and signalling and/ or displaying the occurence of these heart beats, preferably by light signals. According to a special feature of the novel device, means are provided for continuously ascertaining whether sufficient conductivity exists between the body of the patient and the electrodes applied, so as to make sure that the result displayed conforms to the true activity of the heart.

The heart-beat detector according to the present invention is a portable, rugged instrument intended for conclusively determining signs of heart activity in adverse conditions relating both to patient preparation for the test as well as to environmental noise and vibrations. It may be used with full reliability during transportation of the patient in a jolting vehicle (e.g. car, helicopter, or airplain-ambulance) and/or in an environment of noise and vibrations (e.g. in the battle field), which also prevent the use of such classical methods of patient examination as auscultation of the heart. It also replaces other instruments based on ECG monitoring using sound or pointer signalling, which become unuseful or unreliable in noise and vibration conditions or are incapable, due to their inertial properties, to follow rapid events such as heart contractions during tachycardia.

DESCRIPTION OF A PREFERRED EMBODIMENT

The present invention is described by way of illustration with reference to the accompanying drawings. It ought to be clearly understood that this description is by way of example only and ought to be construed in a non-limitative manner. It is clear that many modifications and changes in the different parts and in their arrangement can be resorted to without departing from the scope and spirit of the invention.

Figure 1:
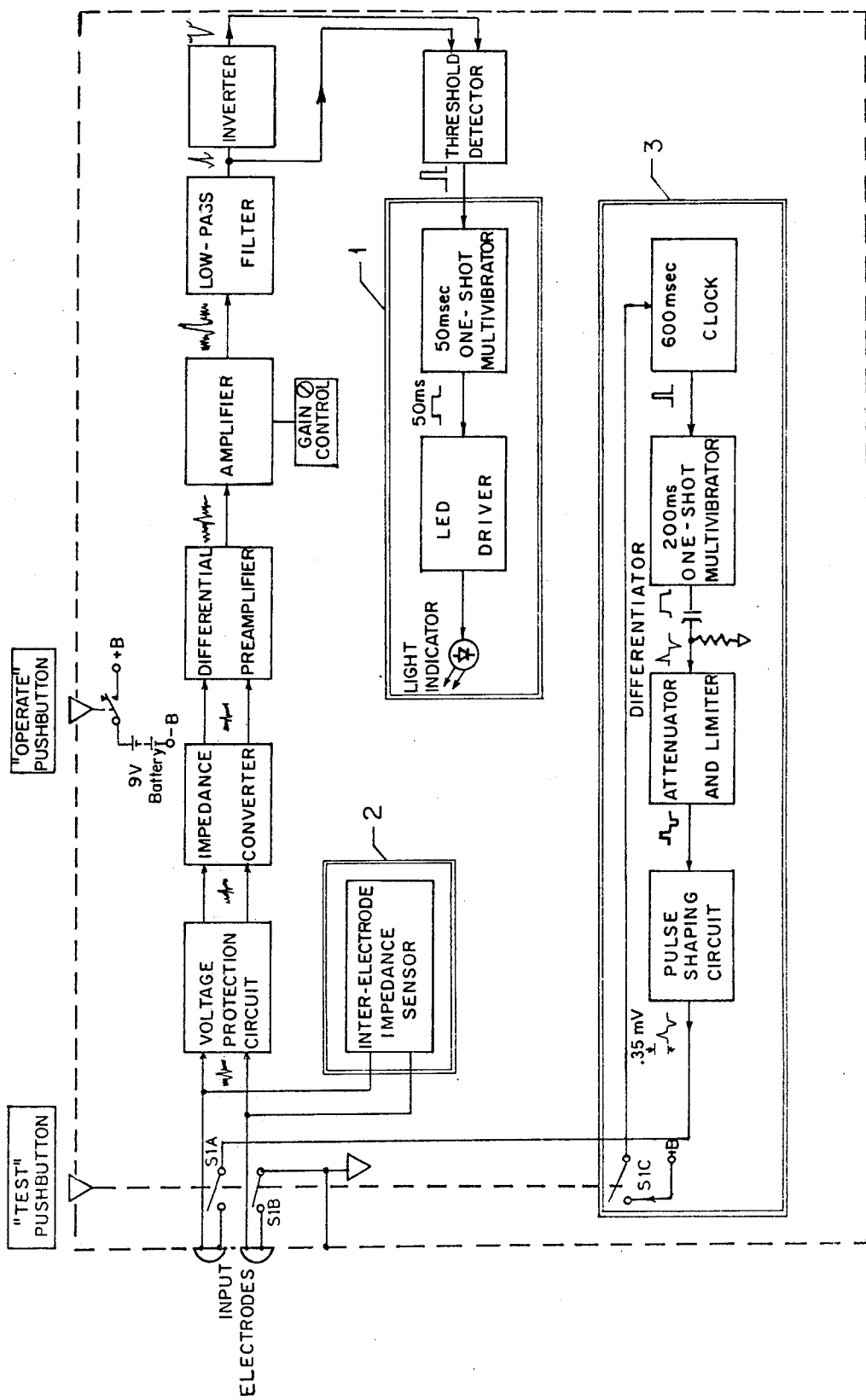
FIG.1 is a block diagram of a system of the invention.

Special sub-systems which are the objects of the present invention, are encircled by double bold lines in FIG.1. The tasks they are fulfilling in the system and their operational principles are presented in the following, along with a general description of the whole system.

The heart-beat detector is devised for use in emergency situations, when the physician treating the patient needs an auxiliary instrument for rapid recognition of the cardiac action, which would facilitate making the decision about the aid to be delivered to the patient. To be useful in fulfilling these tasks, the heart-beat detector is built as a self-contained, simply-operated instrument. Two flexiblymounted electrodes are gently pushed against the chest of the patient, picking up the electric potentials of the heart activity. These signals are led for processing to a high input impedance amplifier followed by filter and inverter stages, which provide at the output relatively noise-free, well-defined ventricular complexes. These further drive a threshold detector and the signalling sub-system. The amplifier gain is adjusted for a sensitivity of the minimum input QRS complexes (e.g. 0.35 mV). The high input impedance of the instrument, its high common mode rejection ratio, and the thorough isolation from environmental interference from power lines, allow for applying the electrodes directly to the skin, without the need of an intermediate electrolytic paste for reduction of the contact resistance. Also, variations of this resistance coming from slight movements of the electrodes during testing in a jolting vehicle or during vibrations, are of no concern for the determination of the genuine heart beats. The favourable response data of the input stages quoted above, allow for using a two electrode pick-up system instead of the conventional 3 electrodes; this fact simplifies the testing procedure, as only two good contact points on the chest have to be found.

One object of the present invention is to use light for signalling. This makes the detection of the heart potentials independent of possible vibrations of the measuring instrument and permits the perceiving of the test results in the presence of acoustical noise. Also, the electro-optical system, being of an inherently low time constant (contrary to electromechanical systems) allows the detection of very rapid heart contractions, such as those occuring during tachycardia (up to 300 beats per minute).

The light-signalling sub-system is presented in the block diagram, FIG.1, within the double-lined block 1.

With each contraction of the heart, a pulse-like signal reaches the input of the signalling sub-system from the output of the threshold detector.

Figure 2:
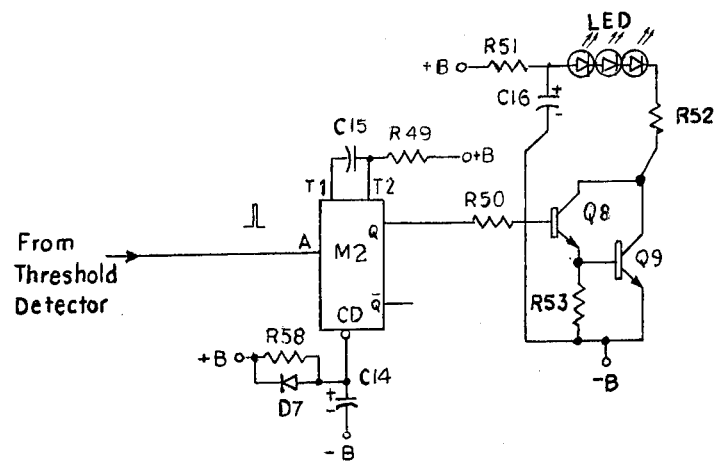
FIG.2 is a wiring diagram of the signalling sub-system of FIG.1

The schematic diagram of the signalling sub-system is shown in FIG. 2.

Referring now to FIG.2, the pulse representing the contraction of the heart is led to the terminal A of a conventional CMOS (complementary-metal-oxide-semiconductor) mono-stable multivibrator M2, triggering the release of a rectangular positive pulse. The duration of the pulse is determined by the capacitor C15 and by the resistor R49, to be, e.g. 50 msec. The resistor R58 and the capacitor C14 provide a pre-setting of the multivibrator with the turning on of the supply battery, to prevent its erroneous operation; after a delay of about 2 seconds, the multivibrator is ready for receiving the triggering pulses. After turning off the supply battery the diode D7 discharges guickly the capacitor C14. The pulse from the output terminal Q of the multivibrator drives through the resistor R50 the Darlington switch-stage containing the transistors Q8 and Q9, which in turn closes the current through the three series-connected LED's (Light Emitting Diode) for the time of the pulse duration and causes lighting of the LED's. Red and green LED's are used to secure a satisfactory perception of the light flashes by the observer under possible adverse environmental illumination; a polaroid protective glass allows satisfactory observation during operation in strong sun-light. The resistors R 51 and R 52 determine the current intensity flowing through the LED's, e.g. 20 mA. The capacitor C16 serves for charge storing, to supply it at a higher current in the first moment of ignition of the LED's. The resistor R53 constitutes a by-pass for the collector-to-base leakage current of the transistor Q9. The LED's flash according to the heart contractions.

Another object of the present invention is the inclusion in the apparatus of a special electrode-body contact sensing sub-system. It serves for continuous evaluation of the interelectrode impedance seen from the input terminals of the heart-beat detector in relation to a given impedance threshold, simultaneously with a monitoring of the heart beats. The interelectrodes impedance measurement is performed in parallel with the heart-beat detection test and is intended to assure maximum accuracy and reliability of the latter. A too high interelectrode impedance (series source impedance) hampers the heart testing by reducing the amplitude of the heart potentials appearing at the input of the heart-beat detector, by increasing the input noise and by facilitating the induction of external interference signals. Once revealed, it may be improved by moistening the electrodes. The electrode body contact sensing adds to the reliability of the heart activity test by distinguishing between lack of ventricular complexes due to poor electrode contact or due to lack of heart action and by avoiding interference signals and artifacts apt to be falsely recognized as heart contractions.

The interelectrode impedance measuring circuit sensor is connected in parallel to the input leads of the heart-beat detector (see: double-lined block 2 in FIG.1). The block and schematic diagrams of the circuit are shown in FIGS. 3 and 4, respectively.

Figure 3:
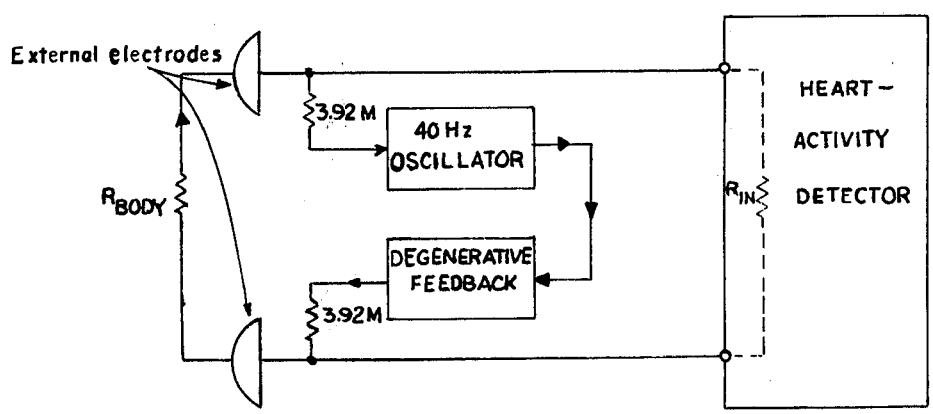
FIG.3 is a block diagram of the interelectrode impedance measuring circuit sensor shown in double-lined block 2 of FIG.1.

Referring to FIG. 3, interelectrode impedance sensor consists of the low requency oscillator (e.g. 40 Hz, within the frequency band of the heart-beat detector) and of the degenerative feedback network, with the input impedance of the heart-beat detector $R_{IN}$ and the interelectrode impedance $R_{BODY}$ constituting a complementing path to the circuit. When the electrodes are open or the interelectrode-impedance with the electrodes at the testing points in the body is higher than a given threshold (e.g. 2 MΩ), the oscillator generates sinusoidal signals (e.g. 40 Hz) which go through all the processing steps within the heart-beat detector and set the signalling LED's in operation. Due to the relatively high frequency (e.g. 40 Hz), the LED's are lit continuously, indicating a too high interelectrode-impedance. Moistening the electrodes with water (or even with saliva) usually reduces this impedance. When the interelectrode-impedance drops or if it is lower than the given threshold (e.g. 2MΩ), the degenerative feedback causes quieting of the oscillator, the continuous operation of the LED's is stopped and the heart-beat detector is ready for testing the heart activity. The interelectrode-impedance measuring circuit interfaces with the two input leads of the heart-beat detector through a high-resistance (several Megohms) (e.g. 3.92 MΩ) balanced configuration, so as not to interfere with the heart activity testing. Referring to FIG. 4, the capacitors C20 and C21 are each connected to one of the input leads of the heart-activity detector, serving for dc decoupling of the bias voltages, while passing the auxiliary e.g. 40 Hz signals generated by the sensor. The resistors R61 and R62 are of high resistance (e.g. 3.92 M) to create a high input impedance of the sensor, to avoid loading of the heart potentials being led in parallel to heart-activity detector. The main part of the sensor is a Wien-bridge oscillator with controlled degeneration feedback. Two inverting amplifiers A1 and A2 are connected in series through decoupling capacitors C23 and C24 to provide 360° phase shift between the input teminal 8 and the output terminal 4. The resistors R65 and R67 establish the bias of the amplifiers. The resistors R63 and R64 constitute a divider network which fixes the amount of positive feedback applied to the frequency determining network. The capacitor C22 and the resistor R68 are in series; the capacitor C25 and the resistor R70 are in parallel, constituting the network which determines the frequency of operation of the Wien-bridge oscillator. The network C25 and R70 instead of being connected directly to ground (as in conventional circuits), is additionally driven by a negative feedback signal. It is led through R61 and C20, $R_{BODY}$ and $R_{IN}$ in parallel, C21 and R62, the inverting amplifier A3 and the resistor R69. The amplification of A3 is determined by the resistor R66 and the impedances R61 and C20, $R_{BODY}$ and $R_{IN}$ in parallel, and C21 and R62. R69 is adjusted (ones in the process of regulation of the heart-beat detector) to provide the amount of negative feedback so that when the interelectrode impedance is smaller than the considered threshold e.g. 2MΩ, the negative feedback signal quenches the Wien-bridge oscillator and testing of the heart activity proceeds normally (without any disturbances). For interelectrode impedances higher than the threshold, e.g. 2MΩ, the Wien-bridge oscillator indeed generates sinusoidal signals of e.g. 40 Hz, which operate the signalling LED's and cause their constant light-emission. The threshold impedance can be established from the practice of heart activity monitoring.

Figure 4:
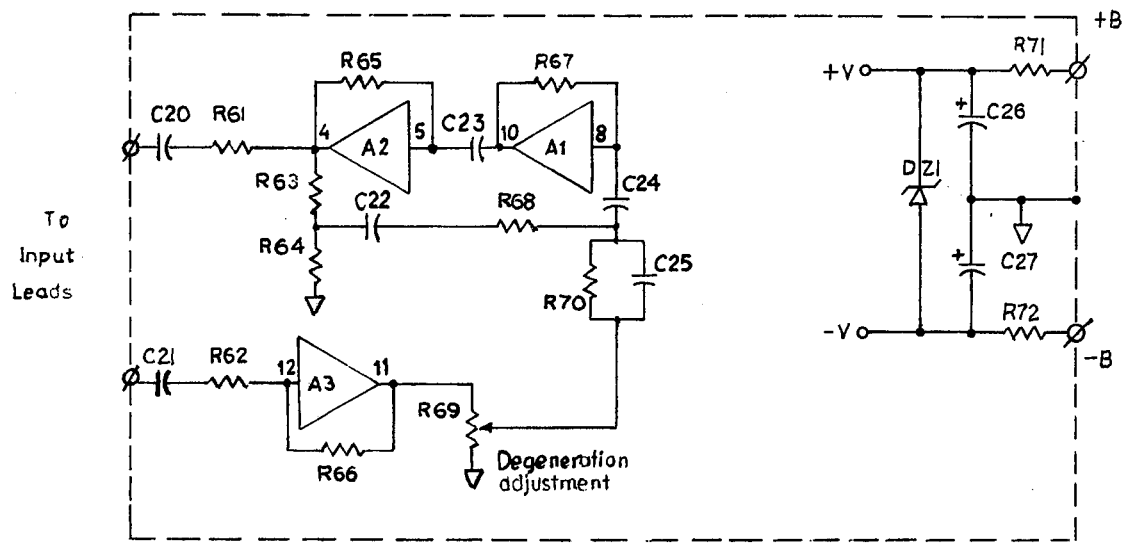
FIG.4 is a wiring diagram of the unit of FIG.3.

Referring further to FIG. 4, the interelectrode impedance sensor is supplied by a stabilized voltage +V—V derived from the battery +B—B through the resistors R71 and R72 and the voltage regulator DZ1. The capacitors C26 and C27 short the a.c. signals coming from the sensor to avoid interference with other circuits of the heart-activity detector.

Still another object of this invention is the addition of the self-testing sub-system to the heart-beat detector (see: double-lined block 3 and "TEST" switch sections S1A and S1B in FIG. 1). The schematic diagram of this circuit is shown in FIG. 5.

Figure 5:
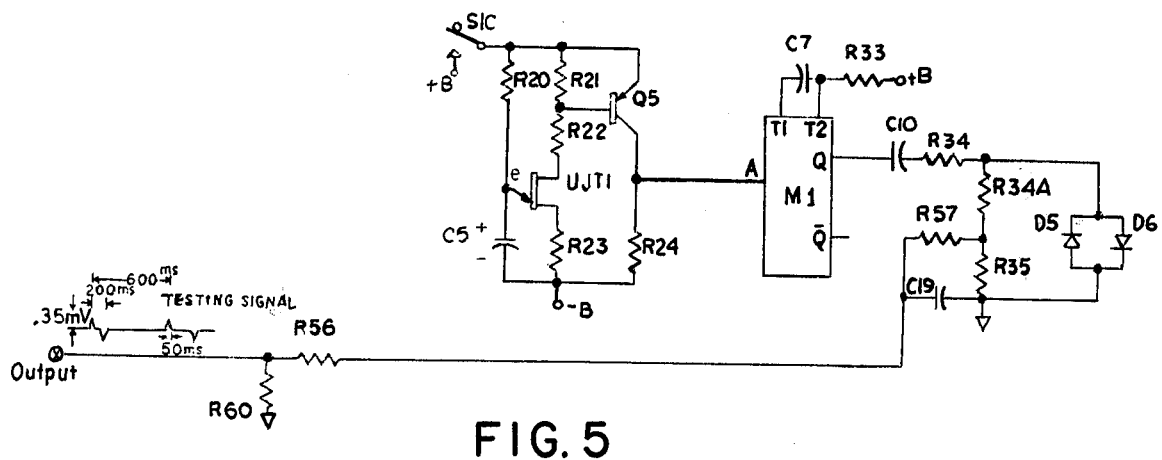
FIG. 5 is a wiring diagram of the self-testing sub-system shown in block 3 of FIG.1.

Referring to FIG. 5 and FIG. 1, the self-testing sub-system is operated from the S1 auxiliary momentary-contact switch. The switch section S1C closes the +B supply to the relaxation oscillator built around the uni-junction transistor UJT1. The resistors R21, R22 and R23 provide the bias for the UJT1, while R21 and R22 serve simultaneously as bias-network elements for the transistor Q5. The resistor R20 and the capacitor C5 determine the rate of pulse generation by the UJT1, e.g. 600 msec. The pulses developing on the R21, switch on the Q5 transistor which in turn supplies a positive driving pulse from across the resistor R24 into the conventional CMOS monostable multivibrator M1 which fires a single rectangular pulse. The resistor R33 and the capacitor C7 determine the duration of the rectangular pulse which appears on the multivibrator's terminal Q, e.g. 200 msec. The rectangular pulse is differentiated by the capacitor C10 and the resistors R34, R34A and R35. Short positive and negative triangular-like pulses are produced at the distance of duration of the differentiated pulse. Further, they are clamped by the two parallel diodes D5 and D6 to provide a constant amplitude, which is independent on battery supply voltage variations. The resistors R34A and R35 constitute also a divider from which the pulses at part of their constant amplitude are led through the shaping network comprising the resistor R57 and the capacitor C19, to another voltage divider consisting of the resistors R56 and R60. The output pulses on R60 are adjusted to be triangular-like, of e.g. 0.35 mV amplitude and of base-width of e.g. 50 msec (simulating the lowest heart contraction QRS complexes); they are coming in pairs (one positive, one negative) at an interval between the component pulses of e.g. 200 msec. at a pair repetition interval of e.g. 600 msec. The testing pulses are led to one of the input electrodes of the hear-beat detector through the switch section S1A (see: FIG. 1), while the other electrode is referred to ground through the other switch section S1B (FIG. 1). Thus, the testing signals pass over the input electrodes, then go through all the processing steps within the heart-beat detector and set in operation the signalling LED's. Flashing the LED-s in accordance to the time schedule of the testing signals indicates that the heart-beat detector, including the electrodes, the complete circuitry and the supply battery, remains in satisfactory condition, ready for testing the heart activity. Change in test flashing may indicate first battery exhaustion, then a circuit or electrode failure. By self-testing, the correct operation of the heart-beat detector is verified.

We claim:

1. A heart-beat detector for continuously monitoring an ECG in emergencies and under adverse conditions, the detector comprising a pair of electrodes which are to be placed in contact with the body of a patient; circuit means coupled to said electrodes and responsive to signal output thereof for extracting QRS complexes and producing signals representative of occurrences of heart-beats; light generating means coupled to said circuit means and responsive to signal output thereof for producing a visible output representative of heart-beats even under adverse conditions of noise, vibrations, ambient light and the like; and means coupled to said electrodes and to said circuit means and responsive to impedance between said electrodes for producing a distinctive input signal to said circuit means upon said impedance exceeding a given level as an indication of too low a conductivity between said electrodes and the body of a patient, said circuit means further producing a distinct output signal upon the occurrence of said distinctive input signal, said light generating means being responsive to said distinct output signal from said circuit means indicative of the occurrence of said impedance exceeding said given value for providing a distinct visible output indicative thereof.

2. A heart-beat detector according to claim 1, wherein said means for producing a distinctive input signal comprises a circuit in parallel with input terminals of said circuit means for producing signals representative of heart-beat, said means for producing a distinctive input signal being connected to said input terminals via a high impedance balanced configuration, so that during normal measurements of the QRS complexes, no interference is caused by said means for producing a distinctive input signal.

3. A heart-beat detector according to claim 2, wherein said means for producing a distinctive input signal comprises an oscillator having a frequency in a range of from about 15 to about 60 cycles per second and including degeneration feedback means coupled via said electrodes for reducing output of said oscillator when good contact is established between said electrodes and the skin of a patient, making possible a correct measurement of the activity of the heart.

4. A heart-beat detector according to claim 1, wherein said light generating means comprise light-emitting diode means for a visual display by light signalling of heart-beat and of the fact that inadequate contact exists between said electrodes and the body of a patient.

5. A heart-beat detector according to claim 1, wherein said detector includes batteries for energization thereof and self-testing sub-system means for testing operative condition of said batteries, said electrodes, said circuit means, and said light generating means.

* * * * *